US00PP14397P29

(12) United States Plant Patent
Hofmann

(10) Patent No.: US PP14,397 P2
(45) Date of Patent: Dec. 23, 2003

(54) VARIETY OF GERANIUM PLANT NAMED 'FIWOWIT'

(50) Latin Name: *Pelargonium x hortorum*
Varietal Denomination: Fiwowit

(75) Inventor: Christa Hofmann, Grossdittmannsdorf (DE)

(73) Assignee: Elsner Pac Jungpflanzen, Dresden (DE)

( * ) Notice: Subject to any disclaimer, the term of this patent is extended or adjusted under 35 U.S.C. 154(b) by 0 days.

(21) Appl. No.: 10/117,887

(22) Filed: Apr. 8, 2002

(51) Int. Cl.[7] ..... A01H 5/00
(52) U.S. Cl. ..... Plt./326
(58) Field of Search ..... Plt./326

(56) References Cited

PUBLICATIONS

GTITM UPOVROM Citation for 'Fiwowit' as per QZ PBR 991801; Dec. 9, 1999.*

PAC–Elsner Website; www.pac–elsner.com; New Varieties Listing 2000.*

GTITM UPOVROM Citation for 'Fiwowit' as per JP PBR 13289; Mar. 9, 2001.*

* cited by examiner

*Primary Examiner*—Kent Bell
(74) *Attorney, Agent, or Firm*—Webb Ziesenheim Logsdon Orkin & Hanson PC

(57) ABSTRACT

A new and distinct geranium plant with a compact habit and white colored flowers having a star-like appearance.

1 Drawing Sheet

Varietal denomination: 'Fiwowit'.
Classification: *Pelargonium×hortorum* (zonal geranium).

BACKGROUND OF THE INVENTION

The present invention comprises a new and distinct cultivar of geranium known by the varietal name 'Fiwowit'. The new variety was discovered in a selective breeding program in Dresden, Germany. The new variety is the result of a combination breeding of unnamed, unpatented selections from the breeding group 6K-80/1. The new variety exhibits the flower color of its heritage, but differs in its compact habit and branching. The new variety was first asexually reproduced by cuttings in Dresden, Germany in 1997. The new variety has been trial and field tested and has been found to retain its distinctive characteristics and remain true to type through successive propagations.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions via cuttings carried out in Dresden, Germany. The color readings were taken on plants grown in 11 cm pots in greenhouses during summer. Plants for the description were nine-months old. Color references are primarily to The R.H.S. Colour Chart of The Royal Horticultural Society of London.

PLANT

Form: Upright.
Height from media surface to top of foliage: 25–28 cm.

Height from media surface to top of umbels: 30–38 cm.
Average plant diameter: Approximately 35 cm.
Growth: Erect, well branched.
Strength: Does not require artificial support.
Roots: 155D, adventive, 3.5 weeks to develop.
Time to produce a flowering plant: 3–4 months.
Leaves: Opposite arrangement; zone present.
- *Length.*—4.5 cm.
- *Width.*—7 cm.

Shape:
- *Overall: Reniform.*
- *Base.*—*Cordate.*
- *Apex.*—Pointed.
- *Margin.*—Entire with deeply incised lobes.
- *Texture.*—Hairy.
- *Color.*—Upper Surface: 137B with zone of 147A. Lower Surface: 137C.

Ribs and veins:
- *Venation.*—Net-veined.
- *Color.*—138B.

Petioles:
- *Color.*—138B.
- *Length.*—5–7 cm.

Stem/branches:
- *Color.*—138B.
- *Overall stem length.*—20–25 cm.
- *Internode length.*—2 cm.
- *Lateral branch length.*—20 cm.

THE BUD (Described at first stage of opening)

Shape:
- *Overall.*—Umbel-shaped.
- *Individual bud.*—Spindle-shaped.

Color: 155C.
Size:
- *Cluster.*—5 cm in diameter.

Individual bud:
*Length.*—0.8 cm.
*Width.*—0.3 cm.

INFLORESCENCE

Flowering: Continuous through summer until frost.
Lastingness of an individual bloom on the plant: 3–4 weeks.
Borne: Umbel; flowers on pedicel; pedicel on peduncle.
Umbel:
*Width.*—8 cm.
*Depth.*—4 cm.
*Number of flowers per umbel.*—50–55.
Flowers:
*Form.*—Zygomorph, single.
*Size.*—Diameter: 2.8–3.4 cm. Depth: 0.5 cm.
*Petals.*—Color: Upper Surface: 155C. Lower Surface: 155D. Size: Length: Upper: 2.0 cm. Lower: 1.6 cm. Width: Upper: 0.4 cm. Lower: 1.1 cm. Shape: Overall: Upper: Narrow/pointed. Lower: Oval-round. Apex: Upper: Pointed. Lower. Round. Base: Pointed. Margin: Upper: Serrated. Lower: Entire. Texture: Smooth.
Petaloids: Absent.
Sepals:
*Shape.*—Overall: Narrow, linear. Apex: Pointed. Base: Fused.
*Color.*—Upper Surface: 144A. Lower Surface: 144B.
*Size.*—Length: 0.7 cm. Width: 0.2 cm.
Pedicel:
*Length.*—2.5–3.0 cm.
*Diameter.*—2 mm.
*Color.*—144B.
Peduncle:
*Length.*—10–15 cm. Diameter: 4–5 mm. Color: 144A.

Disease/pest resistance: No susceptibility to diseases or pests noted to date.

REPRODUCTIVE ORGANS

Stamens:
*Anthers.*—3 mm long.
*Filaments.*—Length: 4 mm. Color: 145D.
*Pollen.*—26A, abundant.
Pistils:
*Number.*—One, five parted.
*Length.*—2 mm.
*Stigma.*—150D.
*Style.*—Length: 0.7 cm. Color: 150D.
Ovaries: Superior, hairy.
*Length.*—0.4 cm.
*Color.*—144 C.
Fruit: If present, maximum 5 per flower, 0.3–0.4 cm long, 165A.

GENERAL CHARACTERISTICS

1. Reniform-shaped leaves.
2. Star-like flower shape.
3. Single flowering.
4. Compact growth.
5. Green zonation of foliage.
6. Tetraploid.
7. Rich Flowering.

I claim:

1. A new and distinct variety of geranium plant substantially as shown and described.

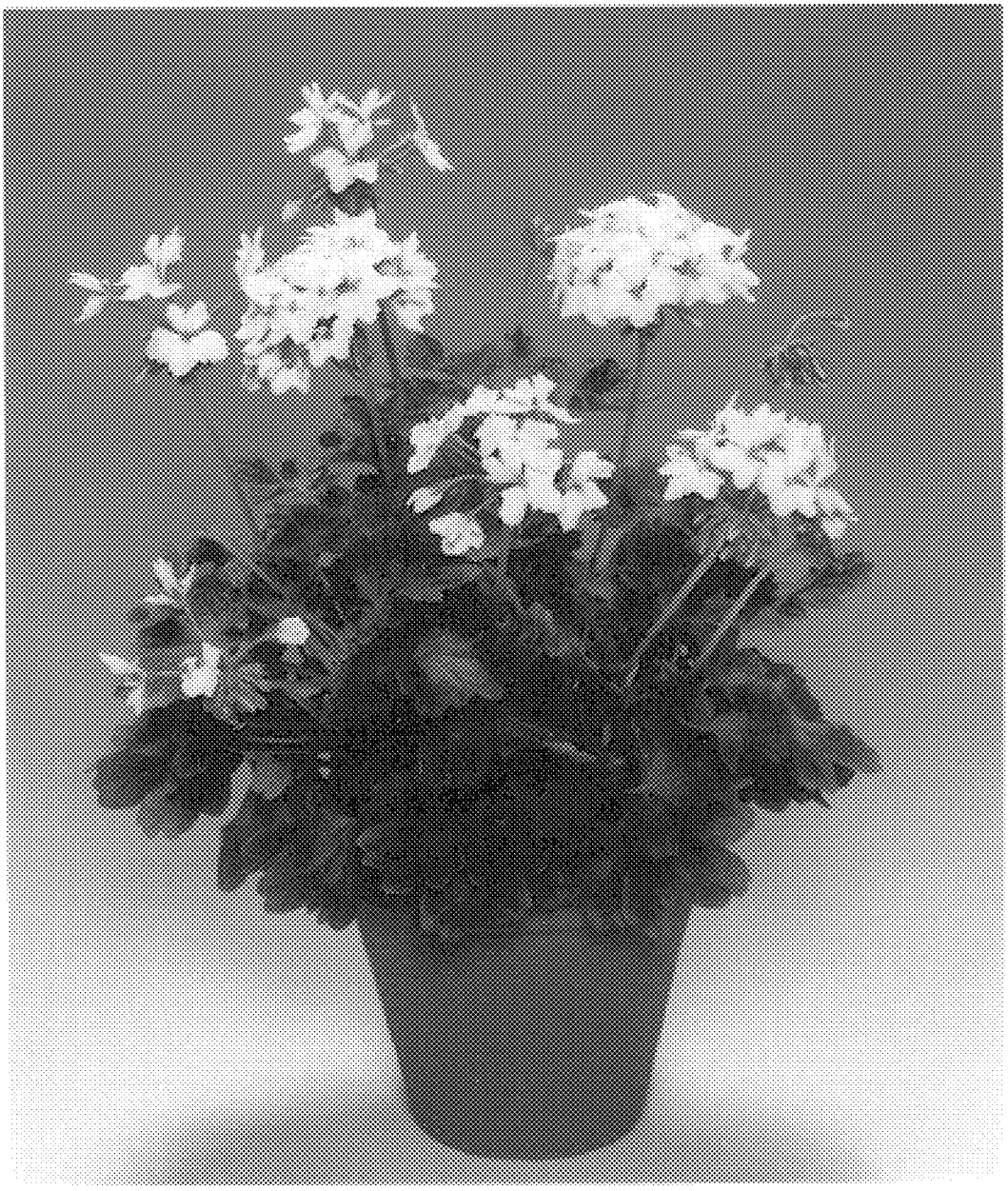

* * * * *